United States Patent [19]

Schwabe et al.

[11] Patent Number: 4,614,758
[45] Date of Patent: Sep. 30, 1986

[54] USE OF PARAFFIN WAXES OR MICROWAXES FOR SILICONE PASTES, AND THE PACKAGING AND USE THEREOF

[75] Inventors: Peter Schwabe; Reiner Voigt, both of Leverkusen, Fed. Rep. of Germany

[73] Assignee: Bayer Aktiengesellschaft, Leverkusen, Fed. Rep. of Germany

[21] Appl. No.: 728,824

[22] Filed: Apr. 30, 1985

[30] Foreign Application Priority Data

May 5, 1984 [DE] Fed. Rep. of Germany ....... 3416694

[51] Int. Cl.$^4$ .............................................. C08K 5/01
[52] U.S. Cl. .................... 524/487; 524/478; 524/480; 524/488; 524/489; 524/859; 524/860; 524/861; 524/862; 206/813
[58] Field of Search ............... 524/478, 480, 488, 489, 524/859, 860, 861, 862, 487

[56] References Cited

U.S. PATENT DOCUMENTS

| | | | |
|---|---|---|---|
| 3,322,709 | 5/1967 | Hammer | 524/480 |
| 3,963,677 | 6/1976 | Enger | 524/478 |
| 4,163,673 | 8/1979 | Dechert | 524/488 |

*Primary Examiner*—Melvyn I. Marquis
*Attorney, Agent, or Firm*—Sprung Horn Kramer & Woods

[57] ABSTRACT

The present invention relates to the use of paraffin waxes or microwaxes in silicone pastes, in particular in kneadable compositions for the production of accurate impressions of teeth. The silicone pastes are preferably cold-vulcanizing two-component silicone rubber systems which are known per se and in which two pastes are mixed and then crosslink after about 2–5 minutes at room temperature.

15 Claims, No Drawings

USE OF PARAFFIN WAXES OR MICROWAXES FOR SILICONE PASTES, AND THE PACKAGING AND USE THEREOF

The present invention relates to the use of paraffin waxes or microwaxes in silicone pastes, in particular in kneadable compositions for the production of accurate impressions of teeth. The silicone pastes are preferably cold-vulcanizing two-component silicone rubber systems which are known per se and in which two pastes are mixed and then crosslink after about 2–5 minutes at room temperature.

Silicone pastes are widely used as impression materials in dentistry. In general, they consist of a silicone oil which is mixed with fillers and is based on a polydimethylsiloxane with terminal hydroxyl groups and can be obtained in various consistencies, depending on the method of application, and a liquid or paste-like hardener component containing a metal salt of a monocarboxylic acid, as the catalyst, and a silicic acid ester, as the crosslinking agent.

These two components are mixed with one another before use and crosslink at room temperature within 2–5 minutes as a result of a polycondensation reaction. Besides the crosslinked silicon rubber, small amounts of alcohol are also formed in this reaction, and these slowly diffuse out of the rubber causing linear shrinkage, which leads to inaccuracies in the impressions.

The linear shrinkage is substantially smaller with vinylsilicone impression materials, which have only been known for a few years. These materials consist of two pastes: a base paste containing silicone oil, filler and crosslinking agent, and a catalyst paste containing silicone oil, filler and catalyst.

The silicone oil here is a polydimethylsiloxane with terminal vinyl groups, the crosslinking agent contains the reactive SiH groups and the catalyst preferably consists of a platinum complex. The greater dimensional accuracy of the impression using this system is also accompanied by the easier metering of the base paste and catalyst paste as a result of the pastes having the same viscosity and the mixing ratio of the two pastes being adjusted to 1:1, and the complete absence of taste or odour of the pastes.

Since various techniques are used in dentistry for taking impressions of jaws bearing all or some of their teeth or no teeth and of the mucous membrane, a range of impression materials with various classes of viscosity is necessary, for example low-viscosity, medium-viscosity, high-viscosity and kneadable compositions. These compositions in each case consist of a base paste and a catalyst paste specifically formulated for the required processing time.

Whilst in the case of the low-viscosity, medium-viscosity and high-viscosity compositions the base paste and the catalyst paste are squeezed out of tubes or cartridges in strands of equal length onto a mixing block and are mixed with a spatula, the base paste and catalyst paste of the kneadable impression material are taken with appropriately labelled metering spoons from cans or cups made of plastic and the lumps of equal size are kneaded with the fingers to give a homogeneous composition. This composition is introduced into an impression spoon and then placed in the mouth of the patient. After a few minutes, the spoon containing the mass which has crosslinked to rubber can be removed from the mouth of the patient. The negative shape of the corresponding jaw situation is then further corrected by using low-viscosity impression material and subsequently cast with an aqueous gypsum slurry, which in the hardened state reproduces the jaw situation as a gypsum model.

On removal of the base paste and catalyst paste and also during mixing of the pastes by kneading with the fingers, it is important that the composition does not stick to the removal spoons or to the fingers and/or leave residues behind. Sticking can be prevented by choosing suitable fillers and by adding paraffin oil. Whilst the sticking effect in the case of silicone impression materials which crosslink by condensation can also partly be prevented with talc, this is not possible with the vinylsilicone impression materials which crosslink by addition, since talc has an adverse influence on the setting properties of the compositions. The addition of paraffin oil is also not completely without problems. On the one hand, an amount of 6–8% by weight is required in the composition to prevent sticking, and on the other hand both the pastes and the impressions exude some of the paraffin oil during storage, i.e. paraffin oil accumulates in the depressions in the surface of the paste or drops of paraffin oil form on the surface of the impressions. The latter can prevent bonding between the hardened kneadable composition and the low-viscosity corrective compound if the correction is carried out only after a prolonged period, and on the other hand can result in defects on the gypsum model. Furthermore, the addition of paraffin oil reduces the necessary adhesion of the composition to the walls of the impression spoons or to the impression spoon which has been treated with adhesive.

According to the invention, these problems are avoided by using paraffin waxes or microwaxes in the pastes. In order to eliminate the tackiness of the pastes, only about 4–5% by weight of paraffin oil and 1.5–5% by weight of paraffin wax or microwax are preferably required in the paste. The paraffin waxes or microwaxes melt in the range from 30°–55° C.; they are thus solid at room temperature, but soften as a result of energy supplied during mixing by kneading. The pastes according to the invention tend to exude the paraffin oil less. Compositions and impressions which are more stable on storage are obtained in this manner, that is to say hardly any drops of paraffin oil form in the paste or on the rubber of the impression, so that a perfect corrective impression may be taken and/or a perfect gypsum model may be produced, even after prolonged storage of the impression.

In addition, the adhesion of the composition to the walls of the impression spoons is improved.

The invention thus relates to the use of paraffin waxes and/or microwaxes for paste-like silicone compositions, the waxes preferably being used in an amount of 1–10% by weight, in particular 1.5–5% by weight, based on the paste, and preferably melting in the range from 30° to 55° C., in particular 35° to 50° C.

The invention moreover also relates to silicone pastes, in particular silicone impression materials, containing such waxes.

The invention also relates to the packaging of the pastes in portion packs, characterized in that the amount of impression material required for an impression is introduced, for example into a deep-drawn plastic film, the film is covered with aluminum foil and the film and foil are welded together.

Preferably, the paraffin waxes and/or microwaxes are used in dental materials which can be hardened at room temperature and are based on polysiloxane. As already mentioned above, a distinction is made here between systems which crosslink by addition and those which crosslink by condensation. Pastes according to the invention which crosslink by the addition system contain, as essential components, (a) organopolysiloxanes with two or more vinyl groups in the molecule, (b) inorganic fillers (untreated or surface-modified), (c) organohydridopolysiloxanes as crosslinking agents, (d) a catalyst to accelerate the addition reaction, (e) paraffin oil, (f) paraffin wax or microwax and, if appropriate, (g) dyestuffs.

The pastes according to the invention which crosslink by the condensation system and contain a catalyst which catalyzes condensation of the polydimethylsiloxane and a crosslinking agent, for example, a liquid or paste-like hardener component consisting of a metal salt of a monocarboxylic acid, and the crosslinking agent is, for example, a silicic acid ester, contain, as essential constituents, (h) organopolysiloxanes with two or more hydroxyl groups in the molecule, (i) fillers, (j) paraffin oil, (k) paraffin waxes or microwaxes and, if appropriate, (i) dyestuffs.

The kneadable silicone pastes according to the invention are distinguished by their storage stability and their freedom from tackiness when the base paste and catalyst paste or when the paste and hardener component are mixed. They are suitable for the production of accurate impressions of teeth because, after the crosslinking paste and catalyst paste have been mixed thoroughly and introduced into the oral cavity and have solidified therein, the impression has been cast with a gypsum slurry and the slurry has hardened to form a model, their reproduction in the gypsum model is true to detail. This good result is achieved because no drops of paraffin oil which interfere with the bonding between the preliminary impression of the kneadable compositions and the corrective impression of the low-viscosity compositions and/or falsify the surface of the gypsum model form on the surface of the impression.

The substances used in the abovementioned pastes which can be hardened at room temperature are known per se.

The silicone oil (a) is a polydimethylsiloxane containing vinyl end groups, the viscosity of which is preferably in the range from 500 to 5,000,000 mPa.s at 20° C.

Examples of suitable fillers (b) are quartz flour and cristobalite flour, calcium sulphate, diatomaceous earth, talc and calcium carbonate. The particle size of the fillers is preferably between 1 and 25μ. Fillers which are too fine-particled can lead to an undesirable structural viscosity of the paste.

The crosslinking agent (c) is a polydimethylsiloxane which has its molecule hydrogen atoms on at least two silicon atoms.

The catalyst (d) is, for example, a platinum complex which has been prepared from hexachloroplatinic-IV acid. These compounds are also known per se.

The paraffin oil (e) comprises of a mixture of alkanes which is liquid at room temperature and has a viscosity of preferably 120–300 mPa.s, particularly preferably 170–230 mPa.s, at 20° C.

The paraffin waxes or microwaxes (f) to be used according to the invention are mixtures of straight-chain and branched alkanes (preferably from $C_{15}$ to $C_{40}$) which melt in the range from preferably 30° to 55° C., in particular 35° to 50° C.

Dyestuffs (g) are preferably employed to differentiate between the base paste and catalyst paste and to control mixing. Inorganic and organic coloured pigments are preferred.

The silicone oil (h) is a polydimethylsiloxane with terminal hydroxyl groups, the viscosity of which is preferably in the range from 500 to 200,000 mPa.s at 20° C.

The fillers (i), the paraffin oil (j), the paraffin wax or microwax (k) and the dyestuffs (l) are the same substances as described above under (b), (e), (f) and (g).

As described above, the kneadable impression materials are marketed in cans or cups made of plastic. In the case of the vinylsilicone impression materials which crosslink by addition, the base paste and catalyst paste are removed from the containers, before use, with appropriately labelled metering spoons and the lumps of equal size are kneaded with the fingers to give a homogeneous composition. The silicone impression material which crosslinks by condensation is also removed from the container by means of a metering spoon, and is mixed with the corresponding amount of paste-like or liquid hardener by kneading with the fingers.

The addition according to the invention of paraffin waxes or microwaxes can lead to pastes which, on the one hand, are too solid at room temperature for removal with a metering spoon but which, on the other hand, acquire the soft, mouldable consistency advantageous for use, as a result of energy supplied during kneading. Also according to the invention, it is advisable for these pastes to be packaged in portion packs by a procedure in which the amount of impression material required for an impression is introduced into a deep-drawn film of plastic (for example of polystyrene, polyethylene, polypropylene and the like), the film is provided with a cover which can easily be destroyed mechanically (for example with an aluminum foil) and the film and cover are welded together. In the case of silicone impression materials which crosslink by condensation, the amount required for an impression is packaged in each case in one portion, and before use the paste is forced through the aluminum foil and kneaded with a corresponding amount of paste-like hardener from a tube or liquid hardener from a bottle. In the case of the vinylsilicone impression material, the particular amount of base paste and catalyst paste required for an impression is correspondingly packaged. Before use, the two pastes are forced through the aluminum foil and kneaded with the fingers.

The examples which follow, in which all parts denote parts by weight, illustrate the invention.

EXAMPLE 1

(Comparison Experiment)

The base paste was prepared by mixing 175 parts of polydimethylsiloxane containing vinyl end groups and with a viscosity of 80,000 mPa.s at 20° C., 50 parts of polydimethylsiloxane containing dimethylhydridosilyl end groups and with a viscosity of 50 mPa.s at 25° C., 650 parts of extremely fine quartz flour with an average particle size of about 4μ, 60 parts of calcium carbonate with an average particle size of about 8μ, 60 parts of paraffin oil with a viscosity of about 180 mPa.s at 20° C. and 5 parts of inorganic coloured pigment in a kneader.

The catalyst paste was prepared by mixing 229.8 parts of polydimethylsiloxane containing vinyl end groups and with a viscosity of 80,000 mPa.s at 20° C., 650 parts of extremely fine quartz flour with an average particle size of about 4μ, 60 parts of calcium carbonate with an average particle size of about 8μ, 60 parts of paraffin oil with a viscosity of 180 mPa.s and 0.2 part of a complex of platinum and divinyltetramethyldisiloxane in a kneader.

Both pastes are mouldable and free from tackiness and easy to knead, but accumulations of paraffin oil form in the depressions of the surfaces of the two pastes on storage for 7 days.

15 g of base paste and 15 g of catalyst paste were kneaded to a homogeneous composition with the fingers in the course of 30 seconds and the composition was introduced into the mouth on an impression spoon under a suitable pressure. Within 5 minutes, the composition hardened to an elastomer. After removal from the mouth, washing with running water and dabbing with cellulose, the impression was kept at room temperature for 24 hours. Thereafter, droplets of paraffin oil had formed on the surface of the impression, which were transferred in the form of depressions onto the gypsum model, produced by casting the impression with a gypsum slurry of 100 parts of calcium sulphate hemihydrate and 30 parts of water and then leaving to stand for 30 minutes, and thus falsified the gypsum model.

A low-viscosity vinylsilicone impression material was introduced, for corrective impression, into an impression which had been prepared as described above and stored for 24 hours and was covered with oil drops, and the whole was introduced into the mouth under a suitable pressure. The composition which had hardened to an elastomer after 5 minutes had no adhesion to the preliminary impression material at the oil-wetted sites after removal from the mouth.

EXAMPLE 2

(According to the Invention)

The base paste was prepared by mixing 190 parts of polydimethylsiloxane containing vinyl end groups and with a viscosity of 80,000 mPa.s at 20° C., 55 parts of polydimethylsiloxane containing dimethylhydridosilyl end groups and with a viscosity of 50 mPa.s, 40 parts of paraffin oil with a viscosity of 180 mPa.s at 20° C., 22 parts of microwax with a solidification point of 43°–45° C. according to DIN 51,556, 688 parts of extremely fine quartz flour with an average particle size of about 4μ, and 5 parts of inorganic coloured pigment in a kneader.

The catalyst paste was prepared by mixing 270 parts of polydimethylsiloxane containing vinyl end groups and with a viscosity of 80,000 mPa.s at 20° C., 40 parts of paraffin oil with a viscosity of 180 mPa.s at 20° C., 22 parts of microwax with a solidification point of 43°–45° C. according to DIN 51,556, 667.8 parts of extremely fine quartz powder with an average particle size of 4 u and 0.2 part of a platinum-siloxane complex in a kneader.

Both pastes were free from tackiness, showed no exudation of paraffin oil after storage for 2 months and had such a firm consistency that they could be removed from the plastic cans with metering spoons only by applying force. Assuming that about 50 ml of impression material are required for impression of a jaw, a 0.4 mm thick film of polypropylene of dimensions 25×12 cm was provided with 2 rows of 5 depressions each with dimensions of 5 cm in diameter and 1.3 cm in depth by deep-drawing. One row of depressions was filled with the base paste and the other was filled with the catalyst paste, the film was then covered with aluminum foil and the film and foil were welded together.

Before taking the impression, one portion each of base paste and catalyst paste were forced through the aluminium foil and mixed by kneading, whereupon the composition became soft and mouldable, without sticking. After 24 hours, the impression had no oil droplets on its surface. The correction material adhered perfectly and the gypsum model had no defects.

EXAMPLE 3

(Comparison Experiment)

A paste was prepared by mixing 210 parts of polydimethylsiloxane containing hydroxyl end groups and with a viscosity of 50,000 mPa.s at 20° C., 80 parts of paraffin oil with a viscosity of 180 mPa.s at 20° C., 100 parts of calcium carbonate, 600 parts of extremely fine quartz flour from Example 1 and 10 parts of titanium dioxide in a kneader.

The paste was mouldable and free from tackiness and was easy to knead. However, accumulations of paraffin oil formed in the depressions of the surface of the paste on storage for 7 days.

25 g of paste and 1 g of a hardener component consisting of dibutyl-tin dilaurate and tetraethoxysilane were kneaded to a homogeneous composition in the course of 30 seconds and the composition was introduced into the mouth on an impression spoon under a suitable pressure. The composition hardened to an elastomer in the course of 5 minutes. After removal from the mouth, washing with running water and dabbing with cellulose, the impression was kept at room temperature for 24 hours. Thereafter, droplets of paraffin oil had formed on the surface of the impression, which were transferred in the form of depressions to the gypsum model, prepared by casting the impression with a gypsum slurry of 100 parts of calcium sulphate hemihydrate and 30 parts of water and leaving to stand for 30 minutes, and thus falsified the gypsum model.

A low-viscosity silicone impression material was introduced for corrective impression into an impression which had been produced as described above and kept for 24 hours and was covered with oil drops, and the whole was introduced into the mouth under a suitable pressure. The composition which had hardened to an elastomer after 5 minutes had no adhesion to the preliminary impression material at the oil-wetted sites after removal from the mouth.

EXAMPLE 4

(According to the Invention)

A paste was prepared by mixing 220 parts of polydimethylsiloxane containing hydroxyl end groups and with a viscosity of 50,000 mPa.s at 20° C., 40 parts of paraffin oil with a viscosity of 180 mPa.s, 30 parts of microwax with a solidification point of 38°–40° C. according to DIN 51,556, 700 parts of extremely fine quartz flour and 10 parts of titanium dioxide in a kneader.

The paste was free from tackiness, showed no exudation of paraffin oil after storage for 2 months and had a somewhat firm consistency. Although it could be removed from the plastic beaker by means of a metering spoon, it was packaged in portions, for the purpose of more convenient handling: 5 depressions with dimensions of 5×5×2 cm were deep-drawn in a 0.4 mm thick polypropylene film with dimensions of 30×6 cm, and were filled with the paste, the film was covered with aluminum foil and the film and foil were welded together.

Before taking the impression, a portion was forced through the aluminum film. On mixing with the hardener component of dibutyl-tin dilaurate and tetraethoxysilane, the paste became soft and mouldable, without sticking. After 24 hours, the impression had no oil droplets on the surface. Adhesion of the corrective compound was perfect, and the gypsum model had no defects.

What is claimed is:

1. A paste-like silicone-containing composition which crosslinks comprising
   (a) a paraffin wax,
   (b) an organopolysiloxane, said organopolysiloxane having two or more vinyl groups when said crosslinking is by an addition system, said organopolysiloxane having two or more hydroxyl groups when said crosslinking is by a condensation system,
   (c) a filler,
   (d) a crosslinking agent, said crosslinking agent being an organohydridopolysiloxane when said crosslinking is by an addition system,
   (e) a paraffin oil and
   (f) a catalyst, said catalyst being a catalyst to accelerate an addition reaction when said crosslinking is by an addition system, said catalyst being a catalyst which catalyzes condensation of said crosslinking agent and said polydimethylsiloxane when said crosslinking is by a condensation system.

2. A composition according to claim 1 wherein said composition contains a paraffin wax which melts in the range of 30° to 55° C.

3. A composition according to claim 2 wherein said paraffin wax melts in the range of 35° to 50° C.

4. A paste-like silicone-containing composition according to claim 1, which crosslinks by a condensation system, wherein the catalyst is a liquid or paste-like hardener component containing a metal salt of a monocarboxylic acid and wherein the crosslinking agent is a silicic acid ester.

5. A composition according to claim 4, containing a polydimethylsiloxane with terminal hydroxyl groups.

6. A composition according to claim 4 containing a polydimethylsiloxane containing terminal vinyl groups.

7. A composition according to claim 5 wherein said paraffin wax is present in said composition in an amount of 1 to 10% by weight.

8. A composition according to claim 6 wherein said paraffin wax is present in said composition in an amount of 1 to 10% by weight.

9. A composition according to claim 7 additionally containing 3 to 5% by weight of paraffin oil.

10. A composition according to claim 8 additionally containing 3 to 5% by weight of paraffin oil.

11. A composition according to claim 7 wherein said paraffin wax comprise a mixture of $C_{15}$ to $C_{40}$ straight-chain or branched alkanes.

12. A composition according to claim 8 wherein said paraffin wax comprise a mixture of $C_{15}$ to $C_{40}$ straight-chain or branched alkanes.

13. A paste-like silicone-containing composition according to claim 1, wherein said filler is an inorganic filler.

14. A paste-like silicone-containing composition according to claim 1, which further includes a dyestuff.

15. A paste-like silicone-containing composition according to claim 1, wherein said catalyst which accelerates the addition reaction is a platinum complex prepared from hexachloroplatinic-IV acid.

* * * * *